(12) United States Patent
Warawa

(10) Patent No.: US 6,407,093 B1
(45) Date of Patent: Jun. 18, 2002

(54) 1,4-DIAZACYCLOHEPTANE DERIVATIVES FOR THE TREATMENT OF NEUROLOGICAL DISORDERS

(75) Inventor: Edward J Warawa, Wilmington, DE (US)

(73) Assignee: Astrazeneca UK Limited, London (GB)

( * ) Notice: Subject to any disclaimer, the term of this patent is extended or adjusted under 35 U.S.C. 154(b) by 0 days.

(21) Appl. No.: 09/555,927

(22) PCT Filed: Jan. 26, 1999

(86) PCT No.: PCT/GB99/00267

§ 371 (c)(1),
(2), (4) Date: Jun. 6, 2000

(87) PCT Pub. No.: WO99/38863

PCT Pub. Date: Aug. 5, 1999

(30) Foreign Application Priority Data

Jan. 29, 1998 (GB) .............................. 9801812

(51) Int. Cl.$^7$ ...................... A61K 31/55; C07D 243/08; A61P 9/10

(52) U.S. Cl. ....................... 514/218; 540/575

(58) Field of Search ........................ 514/218; 540/575

(56) References Cited

FOREIGN PATENT DOCUMENTS

| EP | 0 280 269 | 8/1988 |
|---|---|---|
| EP | 0 452 204 | 10/1991 |
| WO | WO 93/16057 | 8/1993 |

*Primary Examiner*—Brenda Coleman
(74) *Attorney, Agent, or Firm*—Kenneth F. Mitchell

(57) ABSTRACT

Emopamil inhibitors according to formula (I):

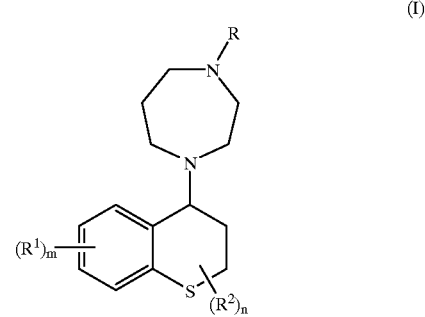

wherein R, $R^1$, m, $R^2$ and n are as defined in the specification, useful in the treatment of neurological disorders, are disclosed. Also disclosed are pharmaceutical compositions containing the compounds, methods for using the compounds and methods for making the compounds.

11 Claims, No Drawings

1,4-DIAZACYCLOHEPTANE DERIVATIVES FOR THE TREATMENT OF NEUROLOGICAL DISORDERS

This application is the national phase of international application PCT/GB99/00267 filed Jan. 26, 1999 which designated the U.S.

The present invention relates to chemical compounds, in particular 1,4-diazacycloheptanes, to processes for their preparation and to chemical intermediates useful in such processes. The present invention further relates to 1,4-diazacycloheptanes, to pharmaceutical compositions containing them and to their use in methods of therapeutic treatment of animals including man, in particular in the treatment of neurological disorders.

Neurological disorders, for which the present compounds are useful, include stroke, head trauma, transient cerebral ischemic attack, and chronic neurodegenerative disorders such as Alzheimer's disease, Parkinson's disease, diabetic neuropathy, amyotrophic lateral sclerosis, multiple sclerosis and AIDS-related dementia.

The compounds useful in the present invention are believed to act by binding with the [$^3$H]-emopamil binding site. Emopamil has classically been thought of as a neuroprotective agent whose efficacy is most likely derived from actions at either voltage-sensitive calcium channels (VSCC) or 5-HT$_2$ receptors. An apparent paradox to this logic is that verapamil, although chemically and pharmacologically very similar to emopamil, is not neuroprotective. While the lack of neuroprotective efficacy by verapamil was initially explained by lack of CNS penetration, recent studies suggest other factors may be involved (Keith et al., Br. J. Pharmacol. 113: 379–384, 1994).

[$^3$H]-Emopamil binding defines a unique high affinity site that is not related to VSCC, is found in the brain, but is most prevalent in the liver (Moebius et al., Mol. Pharmacol. 43: 139–148, 1993). Moebius et al. have termed this the "anti-ischemic" binding site on the basis of high affinity displacement by several chemically disparate neuroprotective agents. In liver, the [$^3$H]-emopamil binding site is localized to the endoplasmic reticulum.

Neuroprotective compounds are known, for example emopamil and ifenprodil, that exhibit high affinity for the [$^3$H]-emopamil binding site. However these are not selective inhibitors and exhibit activity either at neuronal VSCC, the polyamine site of the NMDA receptor (N-Methyl-D-aspartate) and/or the sigma-1 binding site. We have now found a class of compounds that show selective action at the [$^3$H]-emopamil binding site that are neuroprotective in global and focal models of cerebral ischemia without acting directly at either VSCC or NMDA receptors, and consequently exhibit fewer associated side effects than are conventionally seen with either emopamil (hypotension) or ifenprodil (behavioural manifestations). Such compounds are especially useful in treating neurodegeneration resulting from ischemia, for example in Alzheimer's disease, vascular dementia, Parkinson's disease, Huntington's disease and AIDS-related dementia. In another aspect such compounds are especially useful in treating stroke as they provide neuronal protection by preventing neuronal death in the penumbra region surrounding the core infarct.

Accordingly the present invention provides a compound of the formula (I):

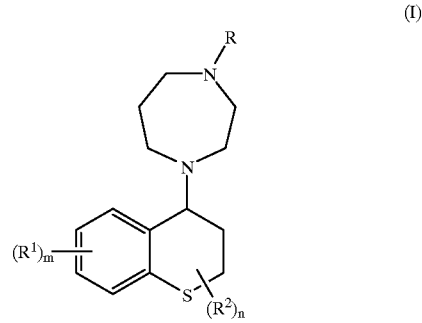

(I)

wherein:
R is hydrogen, $C_{1-10}$alkyl, $C_{3-8}$cycloalkyl, $C_{3-8}$cycloalkyl$C_{1-6}$alkyl, phenyl$C_{1-6}$alkyl or phenyl;
$R^1$ is $C_{1-6}$alkyl, $C_{2-6}$alkenyl, $C_{1-6}$alkoxy, halo, hydroxy, $C_{1-6}$alkanoyl, halo$C_{1-6}$alkyl, cyano or nitro;
m is 0, 1 or 2;
$R^2$ is $C_{1-6}$alkyl;
n is 0, 1 or 2;
wherein any phenyl ring is optionally substituted
or a pharmaceutically acceptable salt or in vivo hydrolysable ester, amide or carbamate thereof.

Any phenyl ring in R may be optionally substituted, for example by up to five substituents, preferably up to three substituents which may be the same or different. Typical substituents include: hydroxy, $C_{1-6}$alkoxy for example methoxy, mercapto, $C_{1-6}$alkylthio for example methylthio, amino, $C_{1-6}$alkylamino for example methylamino, di-($C_{1-6}$alkyl)amino for example dimethylamino, carboxy, carbamoyl, $C_{1-6}$alkylcarbamoyl for example methylcarbamoyl, di-$C_{1-6}$alkylcarbamoyl for example dimethylcarbamoyl, $C_{1-6}$alkylsulphonyl for example methylsulphonyl, arylsulphonyl for example phenylsulphonyl, $C_{1-6}$alkylaminosulphonyl for example methylaminosulphonyl, di-($C_{1-6}$alkyl)aminosulphonyl for example dimethylaminosulphonyl, nitro, cyano, cyano-$C_{1-6}$alkyl for example cyanomethyl, hydroxy$C_{1-6}$alkyl for example hydroxymethyl, amino-$C_{1-6}$alkyl for example aminoethyl, $C_{1-6}$alkanoylamino for example acetamido, $C_{1-6}$alkoxycarbonylamino for example methoxycarbonylamino, $C_{1-6}$alkanoyl for example acetyl, $C_{1-6}$alkanoyloxy for example acetoxy, $C_{1-6}$alkyl for example methyl, ethyl, isopropyl or tert-butyl, halo for example fluoro, chloro or bromo, trifluoromethyl or trifluoromethoxy.

In one aspect the present invention provides a compound of the formula (I) or a pharmaceutically acceptable salt or in vivo hydrolysable amide or carbamate thereof, wherein R is hydrogen, $C_{1-6}$alkyl, $C_{3-8}$cycloalkyl, $C_{3-8}$cycloalkyl$C_{1-6}$alkyl, phenyl$C_{1-6}$alkyl or phenyl; $R^1$ is $C_{1-6}$alkyl, $C_{1-6}$alkoxy, halo, hydroxy, halo$C_{1-6}$alkyl, cyano or nitro; m is 0, 1 or 2; $R^2$ is $C_{1-6}$alkyl; and n is 0, 1 or 2; wherein any phenyl ring is optionally substituted.

Suitably R is hydrogen; $C_{1-10}$alkyl for example methyl, ethyl, n-propyl, isopropyl, n-butyl, isobutyl, pentyl or 2-ethylheptyl. $C_{3-8}$cycloalkyl for example cyclopropyl, cyclobutyl or cyclopentyl; $C_{3-8}$cycloalkyl$C_{1-6}$alkyl for example cyclopropylmethyl, cyclobutylmethyl or cyclopentylmethyl; phenyl$C_{1-6}$alkyl for example benzyl, 2-phenethyl or 3-phenylpropyl.

Favourably R is hydrogen; $C_{1-6}$alkyl for example methyl, ethyl, isopropyl, n-propyl, n-butyl, isobutyl, n-pentyl or 2-methylbutyl; or benzyl. More particularly R is methyl, ethyl, n-propyl, n-butyl or n-pentyl.

Suitably $R^1$ is $C_{1-6}$alkyl for example methyl, ethyl or propyl; $C_{2-6}$alkenyl for example vinyl; $C_{1-6}$alkoxy for example methoxy, ethoxy or propoxy; halo for example bromo, chloro or fluoro; hydroxy; $C_{1-6}$alkanoyl for example formyl or acetyl; halo$C_{1-6}$alkyl for example trifluoromethyl; cyano or nitro.

Preferably $R^1$ is $C_{1-6}$alkoxy for example methoxy or ethoxy or is halo for example bromo, chloro or fluoro. In a particularly preferred aspect, m is one and $R^1$ is methoxy, for example at the 6-position or the 8-position of the 3,4-dihydro-2H-benzothiopyran-4-yl ring system, most preferably at the 8-position. In another particularly preferred aspect, m is one and $R^1$ is bromo or fluoro, for example at the 6-position of the 3,4-dihydro-2H-benzothiopyran-4-yl ring system.

In another particularly preferred aspect m is zero.

Suitably $R^2$ is $C_{1-6}$alkyl for example methyl or ethyl.

In a preferred aspect n is zero.

A particular class of preferred compounds is that of the formula (II):

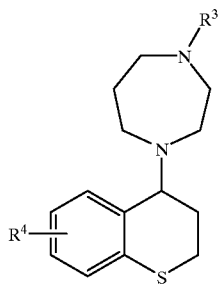

(II)

wherein $R^3$ is hydrogen, $C_{1-6}$alkyl or benzyl, and $R^4$ is hydrogen, $C_{1-6}$alkoxy or $C_{1-6}$alkyl.

Particular compounds of the present invention include those of the Examples hereinafter and N-methyl-N'-(3,4-dihydro-6-fluoro-2H-benzothiopyran-4-yl)homopiperazine.

The compounds of the present invention possess a chiral centre at the 4-position of the 3,4-dihydro-2H-benzothiopyran-4-yl ring system (that is the carbon atom to which the nitrogen containing ring is attached). Other chiral centres may be present when n is one or two and in any of the substituents R—$R^4$.

The present invention covers all enantiomers, diastereoisomers and mixtures thereof that inhibit the [$^3$H]-emopamil binding site.

As mentioned hereinabove, the compounds of the present invention possess a chiral centre at the 4-position of the 3,4-dihydro-2H-benzothiopyran-4-yl ring system. It is preferred that this centre has the S-stereochemistry under the Cahn-Prelog-Ingold sequence rules. It is preferred that any R or S-enantiomer is substantially free of the corresponding S or R-enantiomer, suitably 90%, more suitably 95%, and for example 96%, 97%, 98% or 99% free of the other enantiomer.

Suitable pharmaceutically acceptable salts include acid addition salts such as hydrochloride, hydrobromide, citrate and maleate salts and salts formed with phosphoric and sulphuric acid. In another aspect suitable salts are base salts such as an alkali metal salt for example sodium or potassium, an alkaline earth metal salt for example calcium or magnesium, or organic amine salt for example triethylamine.

In vivo hydrolysable esters, amides and carbamates hydrolyse in the human body to produce the parent compound. Such esters, amides and carbamates can be identified by administering, for example intravenously to a test animal, the compound under test and subsequently examining the test animal's body fluids. Suitable in vivo hydrolysable groups include N-carbomethoxy and N-acetyl.

In order to use a compound of the formula (I) or a pharmaceutically acceptable salt or in vivo hydrolysable ester, amide or carbamate thereof for the therapeutic treatment (including prophylactic treatment) of mammals including humans, it is normally formulated in accordance with standard pharmaceutical practice as a pharmaceutical composition.

Therefore in another aspect the present invention provides a pharmaceutical composition which comprises a compound of the formula (I) or a pharmaceutically acceptable salt or an in vivo hydrolysable ester, amide or carbamate and pharmaceutically acceptable carrier.

The pharmaceutical compositions of this invention may be administered in standard manner for the disease condition that it is desired to treat, for example by oral, topical, parenteral, buccal, nasal, vaginal or rectal administration or by inhalation. For these purposes the compounds of this invention may be formulated by means known in the art into the form of, for example, tablets, capsules, aqueous or oily solutions, suspensions, emulsions, creams, ointments, gels, nasal sprays, suppositories, finely divided powders or aerosols for inhalation, and for parenteral use (including intravenous, intramuscular or infusion) sterile aqueous or oily solutions or suspensions or sterile emulsions. A preferred route of administration is intravenously in sterile isotonic solution.

In addition to the compounds of the present invention the pharmaceutical composition of this invention may also contain, or be co-administered (simultaneously or sequentially) with, one or more pharmacological agents of value in treating one or more disease conditions referred to hereinabove.

The pharmaceutical compositions of this invention will normally be administered to humans so that, for example, a daily dose of 0.05 to 75 mg/kg body weight (and preferably of 0.1 to 30 mg/kg body weight) is received. This daily dose may be given in divided doses as necessary, the precise amount of the compound received and the route of administration depending on the weight, age and sex of the patient being treated and on the particular disease condition being treated according to principles known in the art.

Typically unit dosage forms will contain about 1 mg to 500 mg of a compound of this invention.

Therefore in a further aspect, the present invention provides a compound of the formula (I) or a pharmaceutically acceptable salt or an in vivo hydrolysable ester, amide or carbamate thereof for use in a method of therapeutic treatment of the human or animal body.

In yet a further aspect the present invention provides a method of treating a disease condition wherein inhibition of the [$^3$H]-emopamil binding site is beneficial which comprises administering to a warm-blooded animal an effective amount of a compound of the formula (I) or a pharmaceutically acceptable salt or an in vivo hydrolysable ester, amide or carbamate thereof. The present invention also provides the use of a compound of the formula (I) or a pharmaceutically acceptable salt or an in vivo hydrolysable ester, amide or carbamate thereof in the preparation of a medicament for use in a disease condition.

In another aspect the present invention provides a process for preparing a compound of the formula (I) or a pharmaceutically acceptable salt or an in vivo hydrolysable ester, amide or carbamate thereof which process comprises:

a) reacting a compound of the formula (III) with a compound of the formula (IV):

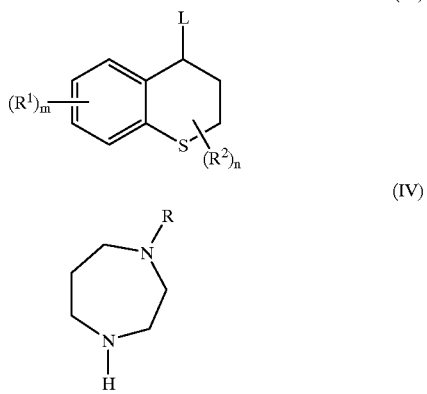

(III)

(IV)

wherein R, R¹, R²⋅ m and n are as hereinbefore defined and L is a leaving group; or b) deprotecting a compound of the formula (V):

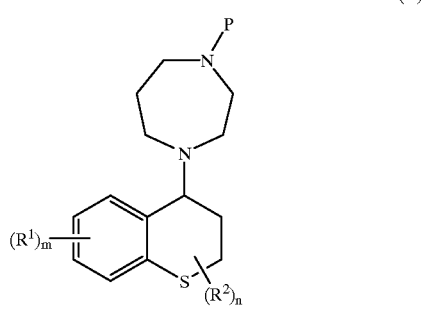

(V)

wherein R¹, R²⋅ m and n are as hereinbefore defined and P is a protecting group for R;

wherein any functional group is protected, if necessary, and:

i) removing any protecting groups;
ii) optionally converting a compound of the formula (I) into another compound of the formula (I);
iii) optionally forming a pharmaceutically acceptable salt or an in vivo hydrolysable ester, amide or carbamate.

Protecting groups may in general be chosen from any of the groups described in the literature or known to the skilled chemist as appropriate for the protection of the group in question, and may be introduced by conventional methods.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower" signifies that the group to which it is applied preferably has 1–4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxyl protecting group may be the residue of an ester-forming aliphatic or araliphatic alcohol or of an ester-forming silanol (the said alcohol or silanol preferably containing 1–20 carbon atoms).

Examples of carboxy protecting groups include straight or branched chain (1–12C)alkyl groups (eg isopropyl, t-butyl); lower alkoxy lower alkyl groups (eg methoxymethyl, ethoxymethyl, isobutoxymethyl); lower aliphatic acyloxy lower alkyl groups, (eg acetoxymethyl, propionyloxymethyl, butyryloxymethyl, pivaloyloxymethyl); lower alkoxycarbonyloxy lower alkyl groups (eg 1-methoxycarbonyloxyethyl, 1-ethoxycarbonyloxyethyl); aryl lower alkyl groups (eg benzyl, p-methoxybenzyl, o-nitrobenzyl, p-nitrobenzyl, benzhydryl and phthalidyl); tri(lower alkyl)silyl groups (eg trimethylsilyl and t-butyldimethylsilyl); tri(lower alkyl)silyl lower alkyl groups (eg trimethylsilylethyl); and (2–6C) alkenyl groups (eg allyl and vinylethyl).

Methods particularly appropriate for the removal of carboxyl protecting groups include for example acid-, base-, metal- or enzymically-catalysed hydrolysis.

Examples of hydroxyl protecting groups include lower alkyl groups (eg t-butyl), lower alkenyl groups (eg allyl); lower alkanoyl groups (eg acetyl); lower alkoxycarbonyl groups (eg t-butoxycarbonyl); lower alkenyloxycarbonyl groups (eg allyloxycarbonyl); aryl lower alkoxycarbonyl groups (eg benzoyloxycarbonyl, p-methoxybenzyloxycarbonyl, o-nitrobenzyloxycarbonyl, p-nitrobenzyloxycarbonyl); tri(lower alkyl)silyl (eg trimethylsilyl, t-butyldimethylsilyl) and aryl lower alkyl (eg benzyl) groups.

Examples of amino protecting groups include formyl, aralkyl groups (eg benzyl and substituted benzyl, p-methoxybenzyl, nitrobenzyl and 2,4-dimethoxybenzyl, and triphenylmethyl); di-p-anisylmethyl and furylmethyl groups; lower alkoxycarbonyl (eg t-butoxycarbonyl); lower alkenyloxycarbonyl (eg allyloxycarbonyl); aryl lower alkoxycarbonyl groups (eg benzyloxycarbonyl, p-methoxybenzyloxycarbonyl, o-nitrobenzyloxycarbonyl, p-nitrobenzyloxycarbonyl); trialkylsilyl (eg trimethylsilyl and t-butyldimethylsilyl); alkylidene (eg methylidene); benzylidene and substituted benzylidene groups.

Methods appropriate for removal of hydroxy and amino protecting groups include, for example, acid-, base-, metal- or enzymically-catalysed hydrolysis, for groups such as p-nitrobenzyloxycarbonyl, hydrogenation and for groups such as o-nitrobenzyloxycarbonyl, photolytically.

Compounds of the formula (I) wherein R is hydrogen may be converted to compounds of the formula (I) wherein R is other than hydrogen by conventional methods of alkylation with an appropriate alkylating agent or by reductive amination. For example an isopropyl group may be prepared by reacting a compound of the formula (I) wherein R is hydrogen with acetone in the presence of a reducing agent such as sodium borohydride or sodium cyanoborohydride. A 2-methylpropyl group or 2-methylbutyl group may be prepared by reacting a compound of the formula (I) wherein R is hydrogen with the corresponding aldehyde in the presence of a reducing agent such as sodium borohydride or sodium cyanoborohydride.

Thus in another aspect the present invention provides a process for preparing a compound of the formula (I) wherein R is $C_{1-6}$alkyl, from a compound of the formula (I) wherein R is hydrogen by reaction with an alkylating agent or by reductive amination.

Pharmaceutically acceptable salts of the compound of the formula (I) may be prepared in any conventional manner for example from the free base and acid. In vivo hydrolysable esters, amides and carbamates may be prepared in any conventional manner.

The reaction between the compounds of the formulae (III) and (IV) is performed in conventional manner. Typically this reaction takes place in organic solvent for example an anhydrous aprotic solvent such as dimethylformamide, dimethylacetamide or tetrahydrofuran. The reaction is generally performed in the presence of a catalyst, such as an iodide salt for example potassium iodide, and is generally performed at ambient or elevated temperature for example 0°–100° C., more preferably 40°–80° C.

In the compounds of the formula (III), L is a conventional leaving group such as halo for example chloro, iodo or bromo; or a tosylate for example p-toluenesulphonyloxy or methanesulphonyloxy.

The compounds of the formula (III) are either known or may be prepared in conventional manner as known to the organic chemist skilled in the art. One convenient manner is to convert the corresponding 4-hydroxy-3,4-dihydro-2H-benzothiopyran to the compound of the formula (III); for example by treating with thionyl chloride in the presence of pyridine to prepare the compound of the formula (III) wherein L is chloro.

Compounds of the formula (V) wherein P is a protecting group convertible to R may be deprotected in standard manner. Any suitable N-protecting group may be used and deprotected in conventional manner. Favourably P is $C_{1-6}$alkoxycarbonyl and such compounds may be converted to compounds of the formula (I) wherein R is methyl for example by treating with a reducing agent such as lithium aluminium hydride. Certain compounds of the formula (V) are also in vivo hydrolysable amides or carbamates of the compounds of the formula (I).

As mentioned hereinabove, the compounds of the present invention possess a chiral centre at the 4-position of the 3,4-dihydro-2H-benzothiopyran ring system and the present invention encompasses the racemate and individual enantiomers. Enantiomers of the compound of the formula (I) may be prepared in conventional manner by resolution of a racemic compound. Alternatively enantiomers of the compounds of the formula (I) may be prepared in analogous manner to the racemates commencing with chiral starting-materials. In yet a further alternative, a chemical intermediate, for example of the formula (III), or the corresponding hydroxy compound, or of the formula (V), may be resolved and subsequently reacted without destroying chirality.

The following biological test methods, data and Examples serve to illustrate the present invention.

-$^3$H-Emopamil Binding to Guinea Pig Liver Membranes

The method of (−)-$^3$H-emopamil binding was a modification of Zech, C., Staudinger R., Mühlbacher, J. and Glossmann, H. Novel sites for phenylalkylamines: characterization of a sodium-sensitive drug receptor with (−)-$^3$H-emopamil. Eur. J. Pharm. 208: 119–130, 1991.

The reaction mixture contained:
Assay buffer: 10 mM Tris-HCl, 0.1 mM phenylmethylsulfonyl fluoride (PMSF), 0.2% bovine serum albumin (BSA), pH 7.4 at 4° C.
Radioligand: 0.96 nM (−)-$^3$H-emopamil (Amersham).
Guinea pig liver membranes: 40 mg/mL original wet weight.
Compounds: 1–300 nM.
Total volume: 500 µL.

This mixture was incubated for 60 minutes at 37° C. The incubation was terminated by filtering with a Brandel Cell Harvester over Whatman GF/C filters that had been soaked for at least 120 minutes in 0.3% polyethylenimine (PEI) and washed three times with 5 mL of wash buffer containing 10 mM Tris-HCl, 10 mM $MgCl_2$, 0.2% BSA, pH 7.4 at 25° C. Specific binding was defined with 10 µM emopamil. In general compounds with an $IC_{50}$ below 300 nM in this test were of interest and for example the compound of Example 5 gave an $IC_{50}$ value of 9 nM.

Guinea-pig Liver Membrane Preparation

Male guinea pigs were sacrificed by $CO_2$ asphyxiation with dry ice. The livers were quickly excised and weighed and rinsed in membrane preparation buffer containing 10 mM Hepes, 1 mM Tris base-EDTA, 250 mM sucrose, pH 7.4. The livers were then minced, homogenized in 10 times volume with a motor driven Teflon-glass homogenizer with three strokes on ice. The homogenate was centrifuged at 1000×g in a SS34 rotor for 5 minutes at 4° C. The supernatant was filtered through 4 layers of gauze and then centrifuged at 8000×g for 10 minutes at 4° C. This resulting supernatant was centrifuged at 40,000×g for 15 minutes at 4° C. The resulting pellet was resuspended in assay buffer and centrifuged again at 40,000×g for 15 minutes at 4° C. This pellet was resuspended in assay buffer (2.5 fold with respect to original wet weight) and homogenized with one stroke with the Teflon-glass homogenizer. Aliquots of 1 mL were stored at −70° C.

-$^3$H-D-888 Binding to Rat Brain Cortical Membranes

The method of $^3$H-D-888 binding was a modification of Reynolds, I. J., Snowman, A. M. and Synder, S. H. (−)-[$^3$H] Desmethoxyverapamil labels multiple calcium channel modular receptors in brain and skeletal muscle membranes: differentiation by temperature and dihydropyridines. J. Pharmacol. Exp. Ther. 237: no.3, 731–738, 1986.

The assay tubes contained the following:
assay buffer: 50 mM Hepes, 0.2% BSA, pH 7.4
radioligand: 1ηM $^3$H-D888 (Amersham)
rat cortical membranes: 6 mg/ml original wet weight
compounds: 0.3–100 µM
Total volume: 1000 µL This mixture was incubated for 60 minutes at 25° C. The assay was terminated by filtering with a Brandel Cell Harvester over Whatman GF/C filters that had been soaked for at least 120 minutes in 0.3% polyethylenamine (PEI) and washed three times with 5 mL of wash buffer containing 20 mM Hepes, 20 mM $MgCl_2$, pH 7.4. Specific binding was measured with 10 µM methoxyverapamil (D-600). This assay was used to determine in vitro selectivity of compounds vs. L-type voltage sensitive calcium channels, i.e high affinity for the $^3$H-D888 binding site would show a lack of selectivity. For example the compound of Example 5 gave an $IC_{50}$ value of about 15,000 nM.

Rat Brain Cortical Membrane Preparation

Male Sprague-Dawley Rats were sacrificed by decapitation and the brains were quickly excised. The cerebellum and brain stem were removed and discarded; and the rest of the brain was rinsed in 320 mM sucrose. The brain was then homogenized in a 10-fold volume of 320 mM sucrose with a motor driven Teflon-glass homogenizer using 10 strokes on ice. The homogenate was spun at 1000×g for 10 minutes at 4° C. in a SS-34 rotor. The supernatant was then spun at 29,000×g for 20 minutes. The resulting pellet was resuspended in membrane buffer (5 mM Hepes, 0.2% BSA, pH 7.4) to a final concentration of 60 mg original wet weight/mL.

Gerbil Global Model of Cerebral Ischemia

Male Mongolian gerbils (Charles River) weighing 60–70 grams are used in these experiments. They are housed in individual cages with food (Purina Rodent Chow) and water vailable ad libitum. The animal room is maintained at 23° C.±2°, and is on an automatic 12 hour light cycle.

The gerbils are brought to the surgical suite and dosed intraperitoneally with the test agent or vehicle, forty five minutes prior to surgery. Drugs are administered at a volume of 5 ml/kg (intraperitoneal). Vehicle is generally saline, with sodium phosphate added to adjust pH, if needed. Forty-five minutes after dosing the gerbils are anesthetized with halothane (3.3%) which is delivered along with oxygen (1.5 L/M) through a face mask. After the gerbils are anesthetized, halothane is continued at a maintenance level of 1.5–2% along with oxygen. The ventral surface of the neck is shaved and cleaned with alcohol. Surgical procedures are carried out on a thermostat-controlled heating pad set to 37° C. An incision is made in the neck, the carotid arteries are dissected away from the surrounding tissue, and isolated with a 5 cm length of Silastic tubing. When both arteries have been isolated they are clamped with microaneurysm clips (Roboz Instruments). The arteries are visually inspected to determine that the blood flow has been stopped. After 5 minutes the clips are gently removed from the arteries and blood flow begins again. A sham control group is treated identically but is not subjected to carotid artery occlusion. The incisions are closed with suture and the gerbils removed from the anesthesia masks and placed on another heating pad to recover from the anesthesia. When they have regained the righting reflex and are beginning to walk around, they are again dosed with the test compound and returned to their home cages. This occurs approximately five minutes after the end of surgery.

Twenty-four hours post ischemia gerbils are tested for spontaneous locomotor activity, using a Photobeam Activity System from San Diego Instruments. They are individually placed in Plexiglas chambers measuring 27.5 cm×27.5 cm×15 cm deep. The chambers are surrounded by photocells, and every time a beam is broken one count is recorded. Each gerbil is tested for two hours, and cumulative counts are recorded at 30, 60, 90, and 120 minutes. Mean counts are recorded for each group and drug groups are compared to control with an ANOVA and Bonferroni post test. After each gerbil is tested it is returned to its home cage. At this time gerbils are also observed for any changes from normal behavior.

For the next two days no specific testing is performed, but the gerbils are observed two to three times per day for any unusual behaviors or obvious neurological symptoms (i.e. ataxia, convulsions, stereotypic behavior). Four days post ischemia the gerbils are sacrificed by decapitation and their brains removed and preserved in 10% buffered formalin. Brains were removed, fixed and stained with hematoxylin and eosin. Under a light microscope, hippocampal fields were observed and graded for damage to the CA1 subfield: 0 to 4 scale, with 0 representing no damage and 4 representing extensive damage.

Transient Focal Ischemia in Rats

The method was as described by Lin, T-N., He, Y. Y., Wu, G., Khan, M. And Hsu, C. Y. Effect of brain edema on infarct volume in a focal model cerebral ischemia model in rats. Stroke 24:117–121, 1993, which model is considered to be relevant to the clinical situation. Male Long-Evans rats 250–350 g were used. Surgery leading to focal ischemia was conducted under anesthesia with 100 mg/kg ketamine and 5 mg/kg i.m. xylazine. Rectal temperature was monitored and maintained at 37.0±0.5 deg C. The right middle cerebral artery (MCA) was exposed using microsurgical techniques. The MCA trunk was ligated immediately above the rhinal fissure with 10–0 suture. Complete interruption of blood flow was confirmed under an operating microscope. Both common carotid arteries were then occluded using nontraumatic aneurysm clips. After a predetermined duration of ischemia (45 min), blood flow was restored in all three arteries. Twenty-four hours post occlusion, rats were killed under ketamine anesthesia by intracardiac perfusion with 200 ml of 0.9% NaCl. The brain was removed and processed with 2% triphenyltetrazolium chloride to identify and quantitate the infarcted brain region. Compounds were administered by intravenous infusion for 4 hours.

In the examples:
a) all nmr spectra were recorded at 300 MHz and were recorded in $CDCl_3$ unless otherwise stated;
b) evaporation of solvents was carried out under reduced pressure;
c) DMF means N,N-dimethylformamide;
d) DMAC means N,N-dimethylacetamide;
e) THF means tetrahydrofuran.

EXAMPLE 1

1-Methyl-4-(3,4-dihydro-2H-benzothiopyran-4-yl) homopiperazine

A 25 ml 3-necked flask equipped with a condenser and magnetic stirring bar and under a nitrogen atmosphere was charged with a solution of N-methylhomopiperazine (0.35 ml; 2.81 mmol) in DMAC (10 ml). Potassium iodide (0.1 g) was added followed by the addition of 4-chloro-3,4-dihydro-2H-benzothiopyran (0.20 g; 1.2 mmol). This solution was then heated at 60° C. overnight, cooled, and partitioned between water and ethyl acetate which was washed with brine and dried with magnesium sulphate. Filtration and evaporation of solvent gave a yellow oil which was distilled by kugelrohr to give the title compound as an oil (0.31 g), bp (air bath temperature) 130–140° C. at 100 mtorr; essentially homogeneous by tlc (silica gel, 89:10:1 $CH_2Cl_2$:$CH_3OH$:$NH_4OH$), $R_f$ 0.46; $^1H$ nmr δ2.37 (s, 3H), 3.82–3.87 (m, 1H), 6.98–7.34 (m, 3H), 7.69–7.71 (d, 1H).

A solution of the above base (0.30 g; 1.15 mmol) in ethanol (5 ml) was treated with maleic acid (0.30 g; 2.59 mmol) and ether (50 ml) was added portionwise. The resulting white solid was collected by filtration and was dried in a drying pistol, 55° C. and 100 mtorr; to give the dimaleate salt of the title compound (0.205 g); mp 117–118° C.

Anal; Calcd. for $C_{15}H_{22}N_2S \cdot 2C_4H_4O_4 \cdot 0.33H_2O$: C, 55.20; H, 6.17; N, 5.59. Found: C, 54.85; H, 6.00; N, 5.59.

4-Chloro-3,4-dihydro-2H-benzothiopyran was prepared as follows:

A 100 ml 3-necked flask equipped with a condenser bearing a nitrogen inlet, an addition funnel and magnetic stirring bar was charged with 4-hydroxy-3,4-dihydro-2H-benzothiopyran (2.1 g; 12.63 mmol) in dry diethyl ether (40 ml). Pyridine (1.0 ml) was added. A solution of thionyl chloride (6.5 ml; 89.0 mmol) in ether (20 ml) was then added dropwise in 30 minutes and stirring continued overnight. The reaction mixture was then poured into ice/water (100 gm) and the organic phase was separated. The aqueous layer was again extracted with ether and the combined extract was washed with brine and dried with magnesium sulphate. Filtration and removal of solvent in vacuo using a rotary evaporator gave a yellow oil (2.35 g); $^1H$ nmr δ2.32–2.42 (m, 1H), 2.57–2.65 (m, 1H), 2.85–2.92 (m, 1H), 3.57–3.68 (t, 1H), 5.31–5.33 (m, 1H), 7.01–7.29 (m, 4H). This material was used without further purification.

EXAMPLE 2

N-(3,4-Dihydro-2H-benzothiopyran-4-yl) homopiperazine

A 100 ml 3-necked flask equipped with a condenser, addition funnel and magnetic stirring bar and under a nitrogen atmosphere was charged with a solution of homopiperazine (3.0 g; 30.5 mmol) in DMAC (35 ml). Potassium iodide (300 mg) was added followed by the addition of a solution of 4-chloro-3,4-dihydro-2H-benzothiopyran (1.15 g; 6.1 mmol) in DMAC (15 ml). This solution was then heated in an oil bath at 60° C. overnight. The reaction mixture was partitioned between water and ethyl acetate, washed with brine and dried with magnesium sulphate. Filtration and evaporation of solvent gave a yellow oil (1.15 g) which exhibited a satisfactory proton nmr spectrum (300 MHz, CDCl$_3$). This material was used without further purification.

EXAMPLE 3

1-Isopropyl4'-(3,4-dihydro-2H-benzothiopyran-4-yl) homopiperazine

A dry 100 ml 3-necked flask under nitrogen was charged with N-(3,4-dihydro-2H-benzothiopyran-4-yl) homopiperazine (1.15 g; 4.6 mmol), tetrahydrofuran (30 ml) and methanol (15 ml). Acetone (6.5 ml; 88.6 mmol) was added. Then sodium cyanoborohydride, (0.50 g; 8.03 mmol) was added as a solid. The solution was stirred and acetic acid (0.60 ml) was added, resulting in a yellow solution. After several hours the content of the flask was partitioned between saturated sodium bicarbonate and ethyl acetate. The aqueous phase was again extracted with ethyl acetate and the combined organic extract was washed with brine and dried with magnesium sulphate. Filtration and removal of solvent in vacuo left an oil (0.85 g) which was kugelrohr distilled to give the title compound as an oil (0.85 g), bp (air bath temperature) 160–170° C. at 70 mtorr.

Anal: Calcd. for $C_{17}H_{26}N_2S$: C, 70.24; H, 9.02; N, 9.64. Found: C, 69.63; H, 8.81; N, 8.88.

The above base (0.70 g; 2.39 mmol) was dissolved in ethanol (10 ml). To this was added portionwise a dispersion of maleic acid (0.70 g; 6.03 mmol) in ether (50 ml) which resulted in the separation of an oil and solid. Trituration gave a white solid which was dried overnight (60° C. at 100 mtorr) to give the dimaleate salt of the title compound (0.99 g), mp 78–79° C.; $^1$H nmr (300 MHz, CD$_3$OD) δ1.33–1.36 (d, 6H), 4.00–4.05 (m, 1H), 6.28 (s, 4H, CH=CH, maleic acid), 7.02–7.11 (m, 3H), 7.67–7.65 (d, 1H).

Anal: Calcd. for $C_{17}H_{26}N_2S.2C_4H_4O_4.0.5H_2O$: C, 56.40; H, 6.64; N, 5.27. Found: C, 56.42; H, 6.63; N, 5.41.

EXAMPLE 4

S(+) N-(3,4-Dihydro-2H-benzothiopyran-4-yl) homopiperazine

S(+) N-(3,4-Dihydro-2H-benzothiopyran-4-yl) homopiperazine was obtained as the first material to elute on subjecting racemic material (5.2 g), prepared as in Example 2, to preparative Chiral Pak AD HPLC resolution using a 90:10:1 hexane:ethanol:diethylamine solvent system. The enantiomeric purity was determined on an analytical scale using hexane:ethanol:diethylamine (90:5:0.05, v/v) and detection at 230 nm. The solution containing this enantiomer was concentrated using a rotary evaporator and the residue was kugelrohr distilled to give a yellow oil (2.10 g), bp (air bath temperature) 135–140° C. at 125 mtorr; $[\alpha]_D^{22}$+60.7° (c=0.84, methanol); 94% ee.

EXAMPLE 5

S(+) 1-Methyl-4-(3,4-dihydro-2H-benzothiopyran-4yl)homopiperazine

A dry 100 ml 3-necked flask equipped with a condenser, addition funnel and magnetic stirring bar was charged with lithium aluminum hydride (0.70 g; 18.4 mmol) and anhydrous THF (20 ml) under a nitrogen atmosphere. S(+) N-Carbethoxy-N'-(3,4-dihydro-2H-benzothiopyran-4-yl) homopiperazine (2.65 g, 8.28 mmol) in THF (20 ml) was added dropwise and the solution was stirred overnight at ambient temperature. Saturated sodium sulphate (25 ml) was added dropwise at a rate amenable to maintaining control of the reaction and the content of the flask was filtered through diatomaceous earth and the solvent was removed in vacuo. The residue was partitioned between water and ether which was dried with magnesium sulphate. Filtration and removal of solvent in vacuo gave an oil (2.30 g) which was kugelrohr distilled to give the title compound (1.83 g) bp (air bath temperature) 135–140° C. at 150 mtorr., essentially homogeneous by tlc (silica gel, $CH_3OH:CH_2Cl_2:NH_4OH$ 10:89:1), $R_f$ 0.25; $[\alpha]_D^{22}$+46.6° (c=0.75, methanol).

To a stirred solution of the above base (1.80 g) in ethanol (10 ml) was added ethanolic HCl (20 ml). Addition of ether (60 ml) resulted in a white precipitate and oil forming. After additional stirring this solid was collected by filtration and was dried overnight in a drying pistol (60° C. at 100 mtorr) to yield the dihydrochloride salt of the title compound (2.04 g), mp 208–209° C.

Anal: Calcd. for $C_{15}H_{22}N_2S.2HCl.0.50H_2O$: C, 52.32; H, 7.31; N, 8.13. Found: C, 52.38; H, 7.17; N, 7.81.

S(+) N-Carbethoxy-N'-(3,4-dihydro-2H-benzothiopyran-4-yl)homopiperazine was prepared as follows:

A dry 100 ml 3-necked flask equipped with a condenser, addition funnel and magnetic stirring bar under a nitrogen atmosphere was charged with of S(+) N-(3,4-dihydro-2H-benzothiopyran-4-yl)homopiperazine (2.05 g; 8.26 mmol) and methylene chloride (25 ml). Triethylamine (1.5 g; 10.76 mmol) was added and the flask was cooled in a Dry Ice/acetone bath. Ethyl chloroformate (1.0 g; 10.4 mmol) in methylene chloride (15 ml) was added dropwise and the mixture was allowed to warm to ambient temperature slowly. After stirring overnight, the content of the flask was partioned between water and methylene chloride, the organic phase was washed with brine and the solution was dried with magnesium sulphate. Filtration and removal of solvent gave a viscous oil (2.7 g), essentially homogeneous by tlc (silica gel, ethyl acetate), $R_f$ 0.66. This material was used without further purification.

EXAMPLE 6

1Benzyl-4'-(3,4-dihydro-2H-benzothiopyran-4-yl) homopiperazine

A dry 100 ml 3-necked flask under nitrogen was charged with N-(3,4-dihydro-2H-benzothiopyran-4-yl) homopiperazine (1.0 g; 4.03 mmol) and treated sequentially with tetrahydrofuran (20 ml), methanol (10 ml), benzaldehyde (4.0 ml; 39.4 mmol), sodium cyanoborohydride, (0.40 g; 6.43 mmol) and acetic acid (0.31 ml) as in Example 3. The resulting material was purified by column chromatography on silica gel (75 g, 60 microns) with ethyl acetate elution to give an oil (1.47 g).

Anal: Calcd. for $C_{21}H_{26}N_2S$: C, 74.51; H, 7.74; N, 8.27. Found: C, 74.46; H, 7.68; N, 8.20.

The above base (1.42 g; 4.22 mmol) was dissolved in ethanol:ether (10 ml, 1:1). To this was added portionwise a dispersion of maleic acid (1.25 g; 10.75 mmol) in ether (30 ml) which resulted in the separation of a solid which was collected by filtration and dried to give the dimaleate salt of the title compound (1.96 g), mp 156–157° C.; $^1$H nmr (300 MHz, $CD_3OD$) δ4.90 (s, 2H, $ArCH_2N$), 6.28 (s, 4H, CH=CH, maleic acid).

Anal: Calcd. for $C_{21}H_{26}N_2S \cdot 2C_4H_4O_4 \cdot 0.2H_2O$: C, 60.65; H, 6.04; N, 4.88. Found: C, 60.49; H, 5.99; N, 4.96.

EXAMPLE 7

1-Isobutyl-4-(3,4-dihydro-2H-benzothiopyran-4-yl)homopiperazine

A dry 100 ml 3-necked flask under nitrogen was charged with N-(3,4-dihydro-2H-benzothiopyran-4-yl)homopiperazine (1.29 g; 5.19 mmol) and treated sequentially with tetrahydrofuran (34 ml), methanol (17 ml), isobutyl aldehyde (6.7 ml; 73 mmol), sodium cyanoborohydride, (0.49 g; 7.8 mmol) and acetic acid (0.38 ml) as in Example 3. The resulting material was purified by kugelrohr distillation to give an oil (1.33 g), bp (air bath temperature) 128°–135° C. at 100 mtorr; $^1$H NMR (300 MHz, $CD_3OD$) δ0.87–0.89 (d, 6H).

Anal: Calcd. for $C_{18}H_{28}N_2S$: C, 71.00; H, 9.27; N, 9.20. Found: C, 70.78; H, 9.22; N, 9.33.

The above base (1.23 g) was dissolved in ethanol (23 ml) and treated with a saturated solution of maleic acid in ether (48 ml) which resulted in the separation of a solid which was collected by filtration and dried to give the dimaleate salt of the title compound (2.03 g), mp 148.2°–148.6° C.; $^1$H NMR (300 MHz, $d_6DMSO$) δ0.94–0.96 (d, 6H, $CH(CH_3)_2$), 6.14 (s, 4H, CH=CH, maleic acid).

Anal: Calcd. for $C_{18}H_{28}N_2S \cdot 2C_4H_4O_4$: C, 58.19; H, 6.76; N, 5.22. Found: C, 58.25; H, 6.67; N, 5.17.

EXAMPLE 8

1-(3-Methylbutyl)4-(3,4-dihydro-2H-benzothiopyran-4-yl)homopiperazine

A dry 100 ml 3-necked flask under nitrogen was charged with N-(3,4-dihydro-2H-benzothiopyran-4-yl)homopiperazine (1.0 g; 4.03 mmol) and treated sequentially with tetrahydrofuran (20 ml), methanol (10 ml), isoamyl aldehyde (5.0 ml; 46.0 mmol), sodium cyanoborohydride, (0.40 g; 6.4 mmol) and acetic acid (0.4 ml) as in Example 3. The resulting material was purified by kugelrohr distillation to give an oil (1.09 g), bp (air bath temperature) 150°–160° C. at 200 mtorr; $^1$H NMR (300 MHz, $CD_3OD$) δ0.88–0.90 (d, 6H).

Anal: Calcd. for $C_{19}H_{30}N_2S$: C, 71.65; H, 9.49; N, 8.78. Found: C, 71.63; H, 9.35; N, 8.55.

EXAMPLE 9

1-n-Propyl4-(3,4-dihydro-2H-benzothiopyran-4yl)homopiperazine

As in Example 5, to lithium aluminum hydride (0.31 g; 8.2 mmol) in anhydrous THF (15 ml) under a nitrogen atmosphere was added dropwise N-(3,4-dihydro-2H-benzothiopyran-4-yl)homopiperazine propionamide (1.25 g, 4.03 mmol) in THF (20 ml) and the solution was stirred overnight at ambient temperature. Workup gave an oil (1.25 g) which was kugelrohr distilled to give the title compound (1.17 g) bp (air bath temperature) 120°–125° C. at 200 mtorr.

The above base (1.16 g) in ethanol (5 ml) was treated with a dispersion of maleic acid (1.2 g; 10.17 mmol) in ether (30 ml). The resulting solid was collected by filtration and dried to give the dimaleate salt of the title compound (1.86 g), mp 116–117.5° C.; $^1$H nmr (300 MHz, $CD_3OD$)δ0.98–1.03 (t, 3H), 4.00–4.04 (m, 1H, ArCHN), 6.28 (s, 4H, CH=CH, maleic acid).

Anal: Calcd. for $C_{17}H_{26}N_2S \cdot 2C_4H_4O_4$: C, 57.46; H, 6.56; N, 5.36. Found: C, 57.15; H, 6.54; N, 5.39.

N-(3,4-dihydro-2H-benzothiopyran-4-yl)homopiperazine propionamide was prepared as follows:

As in Example 5, to N-(3,4-dihydro-2H-benzothiopyran-4-yl)homopiperazine (1.0 g; 4.02 mmol) and triethylamine (1.4 ml; 10.05 mmol) in methylene chloride (20 ml) at ambient temperature was added dropwise propionyl chloride (0.40 ml; 4.6 mmol) in methylene chloride (15 ml) and the mixture was stirred overnight. Workup gave an oil which was essentially homogeneous by tlc (silica gel, ethyl acetate), $R_f$ 0.46, and it was used without further purification.

EXAMPLE 10

Following conventional procedures well known in the pharmaceutical art the following representative pharmaceutical dosage forms containing a compound of formula I can be prepared:

| (a) Tablet | mg/tablet |
|---|---|
| Compound of Formula I | 50.0 |
| Mannitol, USP | 223.75 |
| Croscarmellose sodium | 60 |
| Maize starch | 15.0 |
| Hydroxypropylmethylcellulose (HPMC), USP | 2.25 |
| Magnesium stearate | 3.0 |

| (b) Capsule | mg/capsule |
|---|---|
| Compound of Formula I | 10.0 |
| Mannitol, USP | 488.5 |
| Croscarmellose sodium | 15.0 |
| Magnesium stearate | 1.5 |

(c) Injection

For intravenous administration, a compound of Formula I is dissolved in an isotonic sterile solution (5 mg/ml).

What is claimed is:

1. A compound in accord with formula (I)

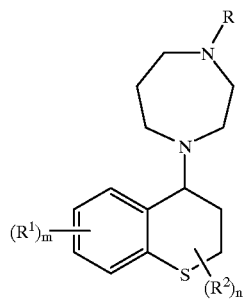

(I)

wherein
R is hydrogen, $C_{1-10}$alkyl, $C_{3-8}$cycloalkyl, $C_{3-8}$cycloalkyl$C_{1-6}$alkyl, phenyl$C_{1-6}$alkyl or phenyl;
$R^1$ is $C_{1-6}$alkyl, $C_{2-6}$alkenyl, $C_{1-6}$alkoxy, halo, hydroxy, $C_{1-6}$alkanoyl, halo$C_{1-6}$alkyl, cyano or nitro;
m is 0, 1 or 2;
$R^2$ is $C_{1-6}$alkyl;
n is 0, 1 or 2;
wherein any phenyl ring is optionally substituted;
or a pharmaceutically-acceptable salt thereof.

2. A compound according to claim 1 wherein
R is hydrogen, $C_{1-6}$alkyl, $C_{3-8}$cycloalkyl, $C_{3-8}$cycloalkyl$C_{1-6}$alkyl, phenyl$C_{1-6}$alkyl or phenyl;
$R^1$ is $C_{1-6}$alkyl, $C_{1-6}$alkoxy, halo, hydroxy, halo$C_{1-6}$alkyl, cyano or nitro;
m is 0, 1 or 2;
$R^2$ is $C_{1-6}$alkyl;
n is 0, 1 or 2; and
wherein any phenyl ring is optionally substituted.

3. A compound according to claim 1 wherein R is hydrogen, $C_{1-6}$alkyl or benzyl.

4. A compound according to claim 3 wherein R is methyl, ethyl, n-propyl, n-butyl, or n-pentyl.

5. A compound according to claim 1 in accord with formula (II):

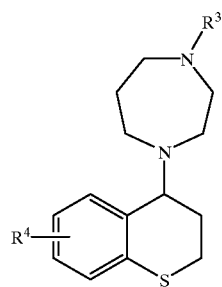

(II)

wherein $R^3$ is hydrogen, $C_{1-6}$alkyl or benzyl and $R^4$ is hydrogen, $C_{1-6}$alkoxy or $C_{1-6}$alkyl.

6. A compound according to claim 1 wherein a chiral center at the 1-position of the 3,4-dihydro-2H-benzothiopyran-4-yl ring has S-stereochemistry.

7. A compound according to claim 1 selected from:
1-methyl-4-(3,4-dihydro-2H-benzothiopyran-4-yl) homopiperazine;
N-(3,4-dihydro-2H-benzothiopyran-4-yl)homopiperazine;
1-isopropyl-4-(3,4-dihydro-2H-benzothiopyran-4-yl) homopiperazine;
S(+) N-(3,4-dihydro-2H-benzothiopyran-4-yl) homopiperazine;
S(+) 1-methyl-4-(3,4-dihydro-2H-benzothiopyran-4yl) homopiperazine;
1-benzyl-4-(3,4-dihydro-2H-benzothiopyran-4-yl) homopiperazine;
1-isobutyl-4-(3,4-dihydro-2H-benzothiopyran-4-yl) homopiperazine;
1-(3-methylbutyl)-4-(3,4-dihydro-2H-benzothiopyran-4-yl) homopiperazine; and
1-n-propyl-4-(3,4-dihydro-2H-benzothiopyran-4yl) homopiperazine.

8. A process for preparing a compound of formula (I)

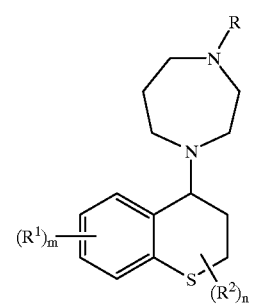

(I)

wherein
R is hydrogen, $C_{1-10}$alkyl, $C_{3-8}$cycloalkyl, $C_{3-8}$cycloalkyl$C_{1-6}$alkyl, phenyl$C_{1-6}$alkyl or phenyl;
$R^1$ is $C_{1-6}$alkyl, $C_{2-6}$alkenyl, $C_{1-6}$alkoxy, halo, hydroxy, $C_{1-6}$alkanoyl, halo$C_{1-6}$alkyl, cyano or nitro;
m is 0, 1 or 2;
$R^2$ is $C_{1-6}$alkyl;
n is 0, 1 or 2;
wherein any phenyl ring is optionally substituted;
or a pharmaceutically-acceptable salt thereof, which process comprises:
a) reacting a compound of formula (III) with a compound of formula (IV):

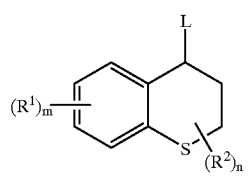

(III)

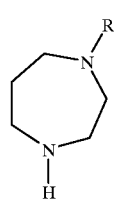

(IV)

wherein L is a leaving group; or b) deprotecting a compound of formula (V):

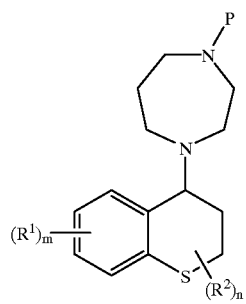
(V)

wherein P is a protected R group, and any functional group is protected, if necessary, and:

i) removing any protecting groups;

ii) optionally converting a compound of formula (I) into another compound of formula (I);

iii) optionally forming a pharmaceutically-acceptable salt.

9. A pharmaceutical composition comprising a compound according to claim 1 together with a pharmaceutically-acceptable carrier.

10. A method of treating an ischemic disease condition wherein inhibition of the [$^3$H]-emopamil binding site is beneficial which comprises administering to a patient in need thereof a therapeutically-effective amount of a compound according to claim 1.

11. A compound according to claim 5 wherein a chiral center at the 1-position of the 3,4-dihydro-2H-benzothiopyran-4-yl ring has S-stereochemistry.

* * * * *